(12) United States Patent
Landrum et al.

(10) Patent No.: US 9,983,116 B2
(45) Date of Patent: May 29, 2018

(54) TESTING A PEEL FORCE OF AN ADHESIVE MEDIUM

(71) Applicant: HEWLETT-PACKARD DEVELOPMENT COMPANY, L.P., Houston, TX (US)

(72) Inventors: Paul C. Landrum, San Diego, CA (US); Xiaoqi Zhou, San Diego, CA (US); Stephen Ledak, Santee, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 169 days.

(21) Appl. No.: 14/899,530

(22) PCT Filed: Jul. 18, 2013

(86) PCT No.: PCT/US2013/051138
§ 371 (c)(1),
(2) Date: Dec. 17, 2015

(87) PCT Pub. No.: WO2015/009309
PCT Pub. Date: Jan. 22, 2015

(65) Prior Publication Data
US 2016/0139031 A1    May 19, 2016

(51) Int. Cl.
*G01N 19/04* (2006.01)

(52) U.S. Cl.
CPC ..... *G01N 19/04* (2013.01); *G01N 2203/0091* (2013.01)

(58) Field of Classification Search
USPC ............................ 73/150 A, 150 R, 827, 830
See application file for complete search history.

(56) References Cited

U.S. PATENT DOCUMENTS

| 2,989,865 | A | * | 6/1961 | Belfour | ................. | G01N 19/04 |
| | | | | | | 73/150 A |
| 3,019,644 | A | * | 2/1962 | Mancini | ................. | G01N 19/04 |
| | | | | | | 73/150 A |
| 4,856,325 | A | | 8/1989 | Tomita et al. | | |
| 4,862,740 | A | * | 9/1989 | Lanier | ................... | G01N 19/04 |
| | | | | | | 73/150 A |
| 4,888,985 | A | * | 12/1989 | Siemer | ................... | G01N 19/04 |
| | | | | | | 73/150 A |
| 4,893,503 | A | | 1/1990 | Kimura et al. | | |
| 5,575,868 | A | | 11/1996 | Mann | | |
| 6,026,680 | A | | 2/2000 | Mann | | |
| 6,050,140 | A | | 4/2000 | Koch | | |
| 6,527,900 | B1 | | 3/2003 | Kreckel et al. | | |

(Continued)

FOREIGN PATENT DOCUMENTS

GB    610232 A    10/1948
GB    742518 A  * 12/1955    ............. G01N 19/04
(Continued)

*Primary Examiner* — Clayton E LaBalle
*Assistant Examiner* — Warren K Fenwick
(74) *Attorney, Agent, or Firm* — Dierker & Kavanaugh, P.C.

(57) ABSTRACT

Testing a peel force of an adhesive medium includes an elevator assembly slidably connected to a column, the elevator assembly includes a connection to a gripper plate, and the gripper plate includes a first slot sized to accommodate a free portion of an adhesive medium and a jammer sized to secure the free portion of the adhesive medium in the first slot.

15 Claims, 4 Drawing Sheets

(56) References Cited

U.S. PATENT DOCUMENTS

| | | | |
|---|---|---|---|
| 6,553,843 | B1 | 4/2003 | Courtade |
| 6,584,858 | B1 | 7/2003 | Mizayawa et al. |
| 7,628,066 | B2 | 12/2009 | Deng et al. |
| 7,739,918 | B1 | 6/2010 | LaPeyronnie et al. |
| 2002/0100334 | A1 | 8/2002 | Goh et al. |
| 2008/0202254 | A1 | 8/2008 | Deng et al. |
| 2010/0239858 | A1* | 9/2010 | Masuko ............... C08G 18/10 428/354 |
| 2012/0103081 | A1* | 5/2012 | Hoshino ............... G01N 19/04 73/150 A |
| 2012/0123700 | A1 | 5/2012 | Tsaur |
| 2016/0161652 | A1* | 6/2016 | Kitagawa ............... B32B 27/30 428/41.8 |

FOREIGN PATENT DOCUMENTS

| | | |
|---|---|---|
| GB | 742518 A | 12/1955 |
| JP | H0192639 A | 4/1989 |
| JP | H11230893 A | 8/1999 |
| JP | 2006-194599 | 7/2006 |
| JP | 2006-337101 | 12/2006 |
| KR | 10-2011-0084723 | 7/2011 |

* cited by examiner

TESTING A PEEL FORCE OF AN ADHESIVE MEDIUM

BACKGROUND

An adhesive medium, such as a self-adhesive film, may adhere to a surface such as a wall. Different adhesive mediums have different adhesive properties. As a result, one adhesive medium may adhere to a particular surface better then another adhesive medium. To determine an adhesive medium's adhesive properties on a particular surface, the adhesive medium is first applied to the particular surface and then removed. The force to remove the adhesive medium from a particular surface is calculated as a peel force. The peel force is used to determine an adhesive medium's adhesive properties.

BRIEF DESCRIPTION OF THE DRAWINGS

The accompanying drawings illustrate various examples of the principles described herein and are a part of the specification. The examples do not limit the scope of the claims.

Throughout the drawings, identical reference numbers designate similar, but not necessarily identical, elements.

DETAILED DESCRIPTION

Figure 1:
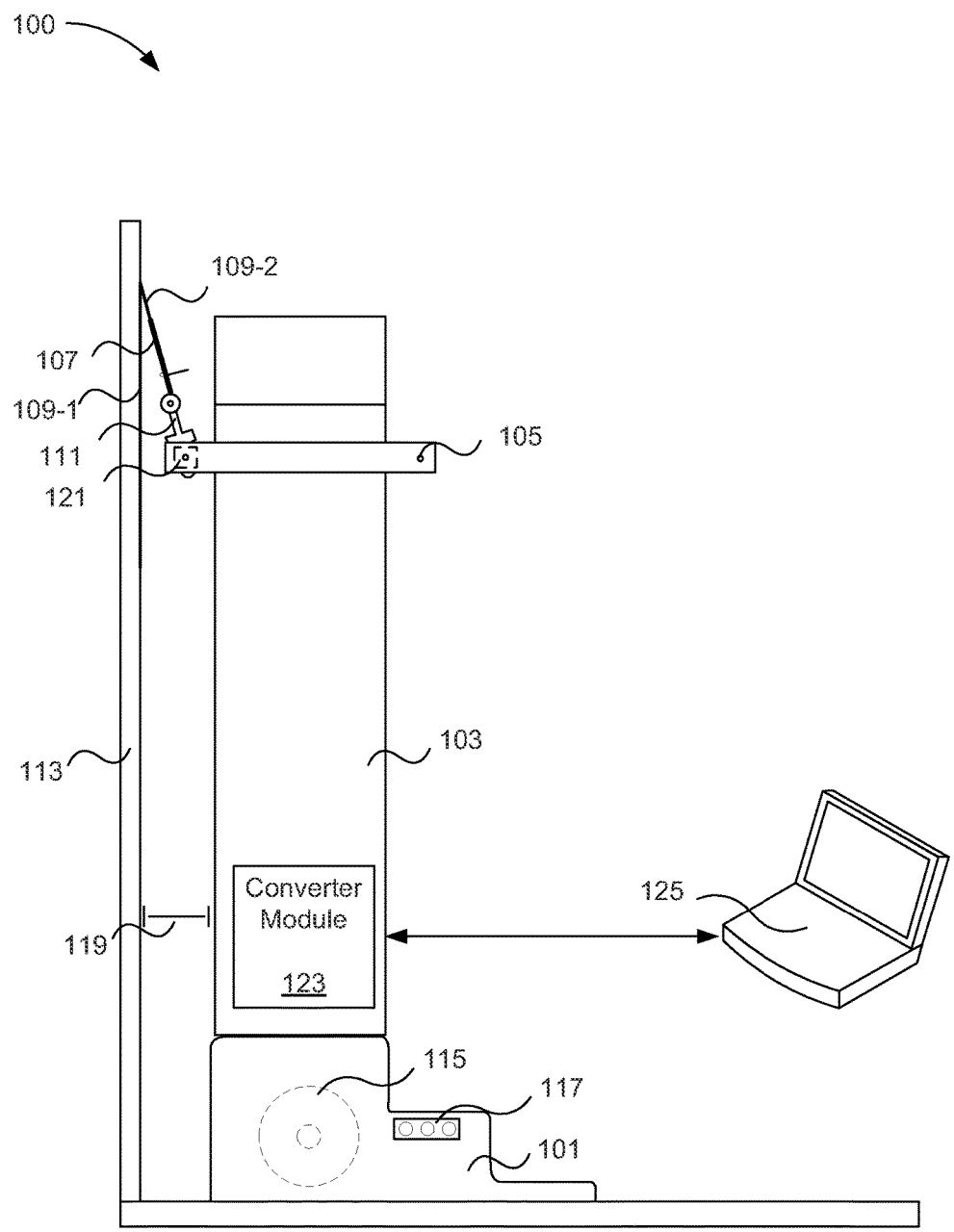
FIG. 1 is a diagram of an example of an adhesive medium tester according to the principles described herein.

To determine an adhesive medium's adhesive properties on a particular surface, accurate information about the adhesive medium's adhesive properties are to be obtained. A laboratory device may be used to obtain an adhesive medium's adhesive properties. The laboratory device may use a small sample size of adhesive medium to determine the adhesive medium's adhesive properties. For example, a first end of the small sample size of adhesive medium is attached to a fixed arm of the laboratory device and a second end of the small sample size of adhesive medium is attached to a moving surface. As the surface moves away from the fixed arm, the small sample size of adhesive medium is removed from the surface. As a result, a peel force may be measured as the small sample size of adhesive medium is removed from the surface.

Although, a laboratory device may be used to measure a peel force, a small sample size of adhesive medium may have a different peel force when compared to a large sample size of the same adhesive medium. As a result, if a large size of adhesive medium is used in a particular application based on testing performed with a small sample size of that medium, the expected peel force for the large size of adhesive medium may be inaccurate. Further, due to the size of a laboratory device, it can be cumbersome to use in a real world environment, for example to test large samples of an adhesive medium.

Additionally, a hand held device may be used to determine an adhesive medium's adhesive properties. The hand held device allows for quick and easy testing of any sized sample of adhesive medium. However, to determine an accurate peel force when testing an adhesive medium's adhesive properties, the hand held device has to remove the adhesive medium at a constant speed as well as a constant angle. As a result, a user using the hand held device may not obtain an accurate peel force of an adhesive medium because the hand held device may not be operated in such a way as to remove the adhesive medium at a constant speed or a constant angle.

The principles described herein include an apparatus for testing a peel force of an adhesive medium. Such an apparatus includes an elevator assembly slidably connected to a column, the elevator assembly includes a connection to a gripper plate, and the gripper plate includes a first slot sized to accommodate a free portion of an adhesive medium and a jammer sized to secure the free portion of the adhesive medium to the first slot. Such an apparatus allows any size sample of adhesive medium to be removed from a surface at a constant speed and a constant angle. As a result, an accurate peel force may be measured to determine an adhesive medium's adhesive properties for any sample size of adhesive medium.

Further, the apparatus can include a sensor support block to secure a load cell sensor to the elevator assembly. Further, the sensor support block swivels on pressed pins to self-align the gripper plate to a constant angle. As a result, an accurate peel force may be measured to determine an adhesive medium's adhesive properties based on the constant angle. More information about the sensor support block will be described in more detail below.

Further, as used in the present specification and in the appended claims, the term "a number of" or similar language is meant to be understood broadly as any positive number comprising 1 to infinity; zero not being a number, but the absence of a number.

In the following description, for purposes of explanation, numerous specific details are set forth in order to provide a thorough understanding of the present systems and methods. It will be apparent, however, to one skilled in the art that the present apparatus, systems, and methods may be practiced without these specific details. Reference in the specification to "an example" or similar language means that a particular feature, structure, or characteristic described in connection with that example is included as described, but may not be included in other examples.

An adhesive medium may be a wall covering, a self-adhesive banner, a self-adhesive film such as polypropylenes, polyethelenes, polyolefins, textiles, other adhesive mediums, and combinations thereof. Further, an adhesive medium may be an off the shelf user applied glue. In one example, the adhesive medium has an adhering portion that is adhered to a target surface and a free portion. As will be described below, the free portion can be gripped by a gripper plate to remove the adhering portion of the adhesive medium off of a target surface.

A peel force is defined as the force needed to overcome the adhesion strength of an adhesive medium and is used to remove the adhering portion of the adhesive medium from a target surface. A peel force may be measured in gram-force, newtons, pound force (lbf), other forces, and combinations thereof.

A target surface may be a surface that an adhesive medium can adhere to such as a wall, a ceiling, a floor, other surfaces, and combinations thereof. Further, a target surface may be made out of concrete, wood, inorganic powdered dry wall, glass, paint, metal, other materials, and combinations thereof. Further, a target surface's properties may be rough, smooth, textured, oily, dusty, painted, wet, dry, other target surface properties, and combinations thereof. As, a result, an adhesive medium's adhesive properties can be measured as a peel force for a number of target surfaces.

A constant angle is used to accurately measure peel force. The angle held constant during measurement of the peel force may be defined as the angle formed between the adhering portion of the adhesive medium and the free portion of the adhesive medium when the free portion of the adhesive medium is held taut by a gripper plate. This angle may be, for example, between 0 degrees and 90 degrees. Again, to accurately measure peel force, this angle is kept constant and unchanged while the adhering portion of the adhesive medium is removed from the target surface. In one example, the constant angle is varied by no more than 0.5 degrees during measurement of peel force.

A constant removal speed is also used to accurately measure peel force. This constant speed may be the speed that the elevator assembly moves along a column. In one example, the elevator assembly moves along the column at 300 millimeters per minute. In another example, the elevator assembly moves along the column at 600 millimeters per minute. Further, the constant speed may be measured to be accurate within 0.5 millimeter per second.

Referring now to the figures, FIG. 1 is a diagram of an example of an adhesive medium tester according to the principles described herein. As mentioned above, to determine an accurate peel force when testing an adhesive medium's adhesive properties, the adhering portion of the adhesive medium is removed from a target surface at a constant speed and a constant angle. As will be described below, an adhesive medium may be applied to a target surface and an adhesive medium tester may be used to remove the adhering portion of the adhesive medium from the target surface. Further, the adhesive medium tester determines an accurate peel force by removing the adhering portion of the adhesive medium from the target surface at a constant speed and a constant angle. As a result, the adhesive medium tester tests the adhesive medium's adhesive properties.

In one example, an adhesive medium tester (100) may include a column (103) rising from a base (101). In this example, an elevator assembly (105) may be slidably connected to the column (103). Further, an electric motor (115) in the base (101) of the adhesive medium tester (100) may be used to move the elevator assembly (105) along the column (103). In one example, the electric motor (115) may be a stepper motor to allow the elevator assembly (105) to move along the column at a constant speed. In another example, the electric motor (115) may be a direct current (DC) motor. In this example, the DC motor allows the elevator assembly (105) to move along the column at a constant speed. In yet another example, the electric motor (115) may be an alternating current (AC) motor. In this example, the AC motor allows the elevator assembly (105) to move along the column at a constant speed.

While in this example an electric motor is used to move an elevator assembly along a column, any appropriate mechanism for moving the elevator assembly along the column may be used. For example, an actuator may be used to move the elevator assembly along the column. In another example, a servo may be used to move the elevator assembly along the column. In yet another example, an electro magnet may be used to move the elevator assembly along the column.

Additionally, while in this example an electric motor is located in the base of the adhesive medium tester, the electric motor or other driver of the elevator assembly may be located in any appropriate location on the adhesive medium tester. For example, the electric motor may be located in the column of the adhesive medium tester. In another example, the electric motor may be located at the top of the adhesive medium tester.

Further, control buttons (117) allow a user using the adhesive medium tester (100) to determine a constant speed of the electric motor (115), As mentioned above, the constant speed of the electric motor (115) affects the constant speed of the elevator assembly (105). In one example, the constant speed of the electric motor may be determined by the number of revolutions of the electric motor (115). As will be described in other parts of this specification, the constant speed of the elevator assembly may affect the peel force of the adhesive medium (109). In one example, the constant speed of the electric motor (115) may be a minimum constant speed. As a result, the elevator assembly (105) moves along the column (103) at a minimum constant speed. In another example, the constant speed of the electric motor (115) may be a medium constant speed. As a result, the elevator assembly (105) moves along the column (103) at a medium constant speed. In yet another example, the constant speed of the electric motor (115) may be a maximum constant speed. As a result, the elevator assembly (105) moves along the column (103) at a maximum constant speed.

While in these examples, three constant speeds are used to allow the elevator assembly to move along the column, any appropriate number of constant speeds may be used. For example, the control buttons may allow the elevator assembly to move along the column at ten different constant speeds during different measurements of peel force. In another example, the adhesive medium tester may use a variable control button. In this example, the variable control button allows the electric motor to rotate at a minimum constant speed, a maximum constant speed, and any constant speed in between.

As mentioned above, the adhesive medium tester (100) includes an elevator assembly (105). In one example, the elevator assembly (105) includes a sensor support block (121) connected to the elevator assembly (105). Further, the sensor support block (121) is connected to a load cell sensor (111). Still further, the load cell sensor (111) is connected to a gripper plate (107). More information about the sensor support block (121), the load cell sensor (111) will be described in later parts of the specification.

As mentioned above, the elevator assembly (105) includes a connection to a gripper plate. In one example, the gripper plate (107) is used to accommodate a free portion (109-2) of the adhesive medium (109). Further, the gripper plate (107) secures the free portion (109-2) of the adhesive medium (109) such that the free portion (109-2) of the adhesive medium (109) does not slip from the gripper plate (107). Thus, the free portion (109-2) of the adhesive medium (109) is attached to the adhesive medium tester (100) using a gripper plate (107). As a result, an accurate peel force may be obtained when removing the adhering portion (109-1) of the adhesive medium (109) from a target surface (113). More information about the gripper plate (107) will be described in later parts of the specification.

The overall operation of the adhesive medium tester (100) will now be described with reference to FIG. 1. In one example, an adhering portion (109-1) of the adhesive medium (109) is applied to a target surface (113). In this example, the target surface (113) may be a wall. As mentioned above, the free portion (109-2) of the adhesive medium (109) is secured to a gripper plate (107) which is attached to an elevator assembly (105). In one example, an electric motor (115) moves the elevator assembly (105) down along the column (103) at a constant speed. As the elevator assembly (105) moves down along the column at a constant speed, the adhering portion (109-1) of the adhesive medium (109) is removed from the target surface (113), In this example, a load cell sensor (111) attached between the gripper plate (107) and a sensor support block (121) is used to determine a peel force needed to remove the adhering portion (109-1) of the adhesive medium (109) from the target surface (113). In one example, the load cell sensor (111) converts the peel force used to remove the adhering portion (109-1) of the adhesive medium (109) from the target surface (113) into a voltage.

In one example, the voltage from the load cell sensor (111) produces a digital output. Further, the digital output from the load cell sensor (111) is gathered by a converter module (123). In this example, the converter module (123) is programmed to interface with a user device (125). In one example, the converter module (123) interfaces with the user device (125) via a Universal Serial Bus (USB) interface. In another example, the converter module (123) interfaces with the user device (125) via a wireless interface.

The user device (125) having a processor and memory, records the data gathered from the converter module (123) in a .csv file format to be used in further analysis of the adhesive medium's adhesive properties. In one example, the .csv file contains a number of data points that represent a number of peel forces recorded while removing the adhesive medium (109). In another example, the .csv file contains one data point that represents an average peel force used to remove the entire adhesive medium (109) from the target surface (113). In another example, the .csv file contains one data point that represents a maximum peel force used to remove the entire adhesive medium (109) from the target surface (113). In yet another example, the .csv file contains one data point that represents a minimum peel force used to remove the entire adhesive medium (109) from the target surface (113).

As mentioned above, a peel force may be affected by the angle at which the adhering portion (109-1) of the adhesive medium (109) is removed from the target surface (113). In one example, the constant angle can be adjusted using a distance (119) between the target surface (113) and the adhesive medium tester (100). For example, if the distance (119) is relatively small, the constant angle at which the adhering portion (109-1) of the adhesive medium (109) is removed is relatively small. Alternatively, if the distance (119) is relatively large, the constant angle at which the adhering portion (109-1) of the adhesive medium (109) is removed is relatively large. As a result, the constant angle at which the adhering portion (109-1) of the adhesive medium (109) is removed can be adjusted to test a peel force of an adhesive medium at a number of constant angles.

Thus, the adhesive medium tester (100) may be used to test a peel force for an adhesive medium (109). Further, the adhesive medium tester (100) can remove the adhering portion (109-1) of the adhesive medium (109) at a number of constant angles and constant speeds to accurately determine a peel force for the adhesive medium (109).

Figure 2:
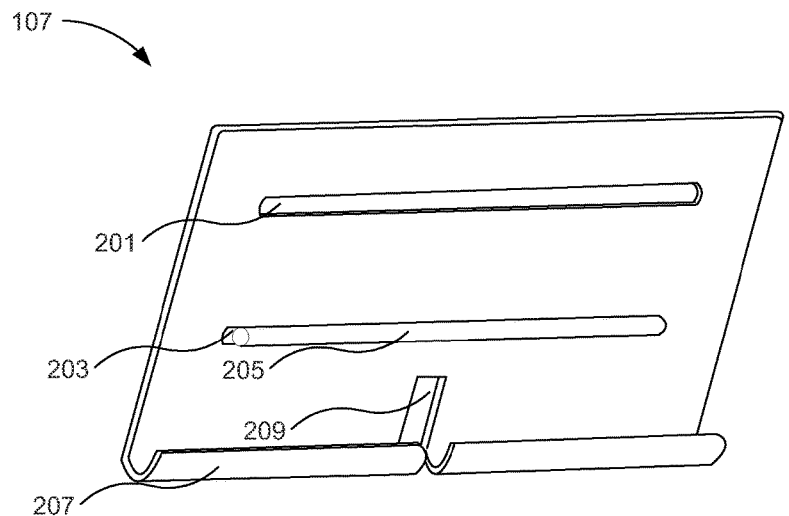
FIG. 2 is a diagram of an example of a gripper plate according to the principles described herein.

FIG. 2 is a diagram of an example of a gripper plate according to the principles described herein. As mentioned above, the gripper plate (107) is used to accommodate a free portion (FIG. 1, 109-2) of the adhesive medium (FIG. 1, 109). Further, the gripper plate (107) secures the free portion (FIG. 1, 109-2) of the adhesive medium (FIG. 1, 109) such that the free portion (FIG. 1, 109-2) of the adhesive medium (FIG. 1, 109) does not slip from the gripper plate (107). As a result, an accurate peel force may be applied and measured.

Turning specifically to FIG. 2, the gripper plate (107) may include a first slot (203) and a second slot (201). In one example, the first slot (203) and the second slot (201) may have a width defined by an opening of the first slot (203) and an opening of the second slot (201). In this example, the width of the first slot (203) and the second slot (201) may be eight inches. As will be described in later parts of this specification, the first slot (203) and the second slot (201) are used to accommodate a number of sample sizes for adhesive mediums up to the width defined by the opening of the first slot (203) and the width defined by the opening of the second slot (201).

As mentioned above, the first slot (203) is sized to accommodate a free portion (FIG. 1, 109-2) of the adhesive medium (FIG. 1, 109). Further, a jammer (205) is sized to secure the free portion (FIG. 1, 109-2) of the adhesive medium (FIG. 1, 109) in the first slot (203). In one example, the jammer (205) is cylindrical in shape. In this example, the jammer (205) is sized to cause an interference fit between the free portion (FIG. 1, 109-2) of the adhesive medium (FIG. 1, 109) and the gripper plate (107), In this example, the jammer (205) is pressed into the first slot (203) after the free portion (FIG. 1, 109-2) of the adhesive medium (FIG. 1, 109) is inserted into the gripper plate (107). More information about inserting free portion (FIG. 1, 109-2) of the adhesive medium (FIG. 1, 109) into the gripper plate (107) will be described in later parts of this specification. Further, the interference fit between the free portion (FIG. 1, 109-2) of the adhesive medium (FIG. 1, 109) and the gripper plate (107) is such that the free portion (FIG. 1, 109-2) of the adhesive medium (FIG. 1, 109) does not slip from the gripper plate (107).

While in this example the jammer is cylindrical in shape, a jammer may be rectangular, round, triangular, other shapes, to cause an interference fit between the free portion of the adhesive medium and the gripper plate. As a result, the jammer secures the free portion of the adhesive medium to the gripper plate.

The gripper plate (107) further includes a hook bend (207) at the end of the gripper plate (107) with a receptacle (207). As will be described in later parts of this specification, the hook bend (207) at the end of the gripper plate (107) with the receptacle (209) allows a load cell sensor and a pull rod to be attached to the gripper plate. As a result, the gripper plate (107) may be easily removed from the elevator assembly (FIG. 1, 105) to accommodate a number of differently sized gripper plates to accommodate a number of differently sized sample adhesive mediums.

While in this example the gripper plate has a first slot and a second slot, a gripper plate may have any appropriate number of slots such that the free portion of the adhesive medium does not slip from the gripper plate. For example, the gripper plate may have five slots that are used to accommodate the free portion of the adhesive medium. Further, while in this example the gripper plate uses one jammer to secure the free portion of the adhesive medium to the gripper plate, any appropriate number of jammers may be used to secure the free portion of the adhesive medium to the gripper plate. For example, a first jammer may be inserted into a first slot on the gripper plate and a second jammer may be inserted into a second slot on the gripper plate.

Figure 3:
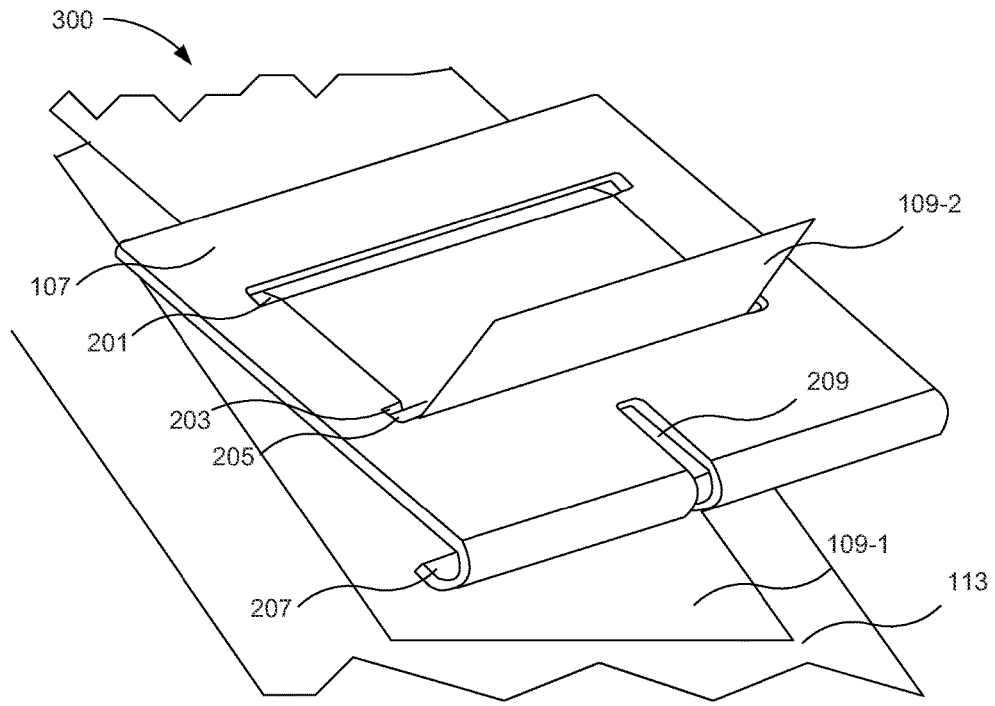
FIG. 3 is a diagram of an example of a gripper plate accommodating an adhesive medium according to the principles described herein.

FIG. 3 is a diagram of an example of a gripper plate accommodating an adhesive medium according to the principles described herein. As mentioned above, the gripper plate (107) is used to accommodate a free portion (109-2) of the adhesive medium (109). Further, the gripper plate (107) secures the free portion (109-2) of the adhesive medium (109) such that the free portion (109-2) of the adhesive medium (109) does not slip from the gripper plate (107). As a result, an accurate peel force may be obtained.

Turning specifically to FIG. 3, in one example, the free portion (109-2) of the adhesive medium (109) is first inserted into the second slot (201) as shown in FIG. 3. The second slot (201) provides additional bends in the free portion (109-2) of the adhesive medium (109) such that the friction between the gripper plate (107) and the free portion (109-2) of the adhesive medium (109) is increased. As a result, the second slot (201) helps to secure the free portion (109-2) of the adhesive medium (109) to the gripper plate (107). The free portion (109-2) of the adhesive medium (109) is then laid over the first slot (203). In this example, the free portion (109-2) of the adhesive medium (109) is laid past the first slot (203). Next, the jammer (205) is pressed into the first slot (203) as shown in FIG. 3. As a result, the free portion (109-2) of the adhesive medium (109) is secured to the gripper plate (107) such that the free portion (109-2) of the adhesive medium (109) does not slip from the gripper plate (107).

Additionally, the gripper plate (107) may accommodate a number of differently sized sample adhesive mediums. In one example, the free portion (109-2) of the size sample of the adhesive medium (109) that can be inserted into the gripper plate (107) depends on a width defined by an opening of the first slot (203) and a width defined by an opening of the second slot (201). For example, the width of the first slot (203) and the second slot (201) may be eight inches. As a result, the free portion (109-2) of the adhesive medium (109) having a width of eight inches may be inserted into the first slot (203) and the second slot (201) of the gripper plate (107). Further, the free portion (109-2) of the adhesive medium (109) having a width of less than eight inches may be inserted into the first slot (203) and the second slot (201) of the gripper plate. As a result, the gripper plate (107) may accommodate a free portion (109-2) of the adhesive medium (109) of eight inches or less.

While in this example the width defined by an opening of the first slot and the second slot is eight inches, the width defined by an opening of the first slot and the second slot may be greater or less than eight inches. For example, the width defined by an opening of the first slot and the second slot may be thirteen inches. In another example, the width defined by an opening of the first slot and the second slot may be four inches.

Figure 4:
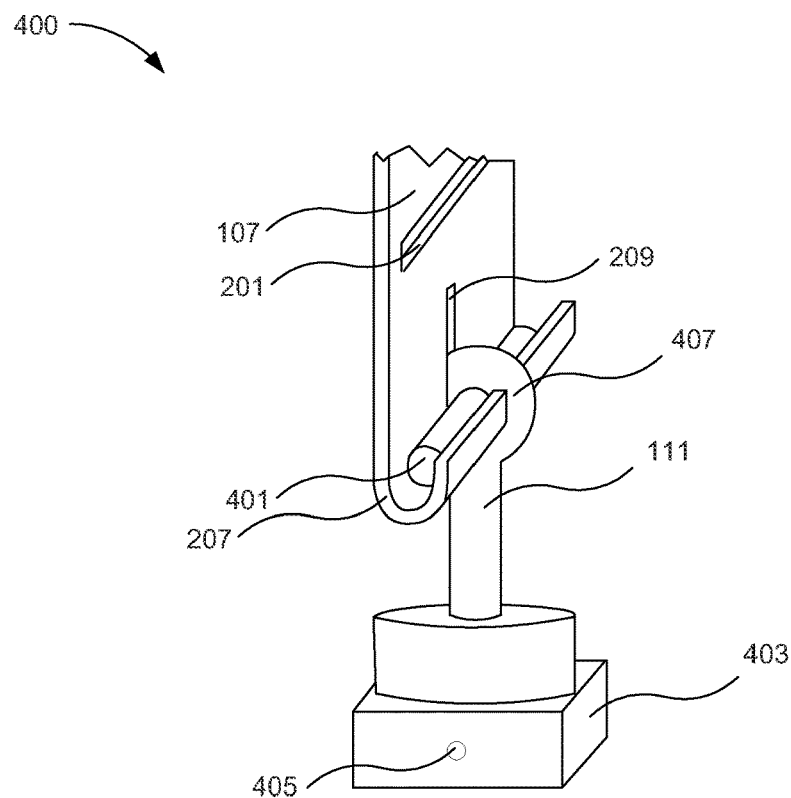
FIG. 4 is a diagram of an example of a pull rod engaging a gripper plate according to the principles described herein.

FIG. 4 is a diagram of an example of a pull rod engaging a gripper plate according to the principles described herein. As mentioned above, the hook bend (207) at the end of the gripper plate (107) with the receptacle (207) allows a load cell sensor (111) and a pull rod (401) to be attached to the gripper plate (107). As a result, the gripper plate (107) may be easily removed from the elevator assembly (FIG. 1, 105) to accommodate a number of differently sized gripper plates to accommodate a number of differently sized sample adhesive mediums.

Turning specifically to FIG. 4, a pull rod (401) is inserted into a receiving portion (407) defined by an opening of the load cell sensor (111). In this example, the pull rod (401) is slightly smaller in diameter than the opening defined by the receiving portion (407) of the load cell sensor (111). As a result, the pull rod (401) may be easily inserted or removed from the opening defined by the receiving portion (407) of the load cell sensor (111). In another example, the pull rod (401) is secured to the receiving portion (407) of the load cell sensor (111) such that the pull rod (401) cannot be easily inserted or removed from the receiving portion (407) of the load cell sensor (111).

The load cell sensor (111) with the pull rod (401) is inserted into a receptacle (209) in the gripper plate (107). The receptacle (209) allows the load cell sensor (111) with the pull rod (401) to clear the hook bend (207), such that the load cell sensor (111) with the pull rod (401) may rest at the bottom of the hook bend (207), As a result, the load cell sensor (111) with the pull rod (401) may engage the gripper plate (107). As mentioned above, when the gripper plate (107) removes a free portion (FIG. 1, 109-2) of the adhesive medium (109), a load is placed on the load cell sensor (111).

In one example, the load cell sensor (111) converts the peel force into a voltage. For example, while removing a six inch wide adhering portion (FIG. 1, 109-1) of an adhesive medium (FIG. 1, 109) from a target surface (FIG. 1, 113) at 300 millimeters per minute, an average peel force of 0.684 pound force (lbf) may be used to remove the adhering portion (FIG. 1, 109-1) of the adhesive medium (FIG. 1, 109) from the target surface (FIG. 1, 113). In this example, the 0.684 pound force (lbf) is applied to the load cell sensor (111). The load cell sensor (111) converts the 0.684 pound force (lbf) into an average volt reading. Further, the average volt reading is then converted back into pound force by the converter module (FIG. 1, 123).

As mentioned above, a user device (FIG. 1, 125) records the data gathered from the converter module (FIG. 1, 123) in a .csv file format to be used in further analysis of the adhesive medium's adhesive properties. In this example, an adhesive medium having an average peel force of 0.684 pound force (lbf) may indicate the adhesive medium has a low tack adhesive property. As a result, the adhering portion of the adhesive medium is easily removed from the target surface.

In another example, a peel force is measured by the load cell sensor (111) at one second intervals for thirty seconds. As a result, thirty peel forces are measured from the load cell sensor (111). For example, while removing a six inch wide adhering portion (FIG. 1, 109-1) of an adhesive medium (FIG. 1, 109) at 300 millimeters per minute from a target surface (FIG. 1, 113), a first peel force at one second is measured to be 0.04 lbf. Further, a fifteenth peel force at fifteen seconds is measured to be 1.77 lbf. Still further, a thirtieth peel force at thirty seconds is measured to be 2.01 lbf. In this example, the adhesive medium has an average peel force of 1.558 lbf. As mentioned above, a user device (FIG. 1, 125) records the data gathered from a converter module (FIG. 1, 123) in a .csv file format to be used in further analysis of the adhesive medium's adhesive properties. In this example, an adhesive medium having an average peel force of 1.558 pound force (lbf) may indicate the adhesive medium has a high tack adhesive property. As a result, the adhering portion of the adhesive medium is not easily removed from the target surface.

While this example uses a load cell sensor to determine a peel force for an adhesive medium, any appropriate sensor may be used to determine the peel force for the adhesive medium. For example, a piezoelectric crystal force transducer, a strain gauge load cell, a pressure induced force transducer, other force transducers, and combinations thereof may be used to determine the peel force for the adhesive medium.

Figure 5:
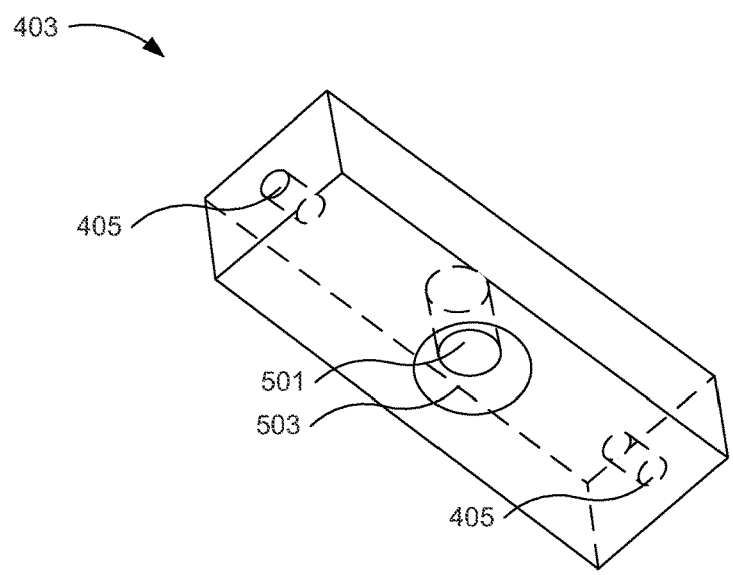
FIG. 5 is a diagram of an example of a sensor support block according to the principles described herein.

FIG. 5 is a diagram of an example of a sensor support block according to the principles described herein. As mentioned above, the sensor support block (403) swivels on pressed pins (405) to self-align the gripper plate to a constant angle. As a result, an accurate peel force may be measured to determine an adhesive medium's adhesive properties based on the constant angle. Further, when a force is applied to the gripper plate (107), the constant angle may be unchanged while removing the adhesive medium from a target surface.

In one example, a portion of the load cell sensor (FIG. 1, 111) passes through a receiver (501) defined by an opening in the sensor support block (403). In this example, the portion of the load cell sensor (FIG. 1, 111) is held captive in the beveled impression (503) of the receiver (501). As the tension increases on the load cell sensor (FIG. 1, 111), the load cell is compress against the beveled impression (503) on the receiver (501). As a result, the load cell sensor (FIG. 1, 111) converts the force applied to the load cell sensor (FIG. 1, 111) applied by the sensor support block (403) into a voltage. As mentioned, a converter module (FIG. 1, 123) is used to read the voltage and converts the voltage into a force.

Figure 6:
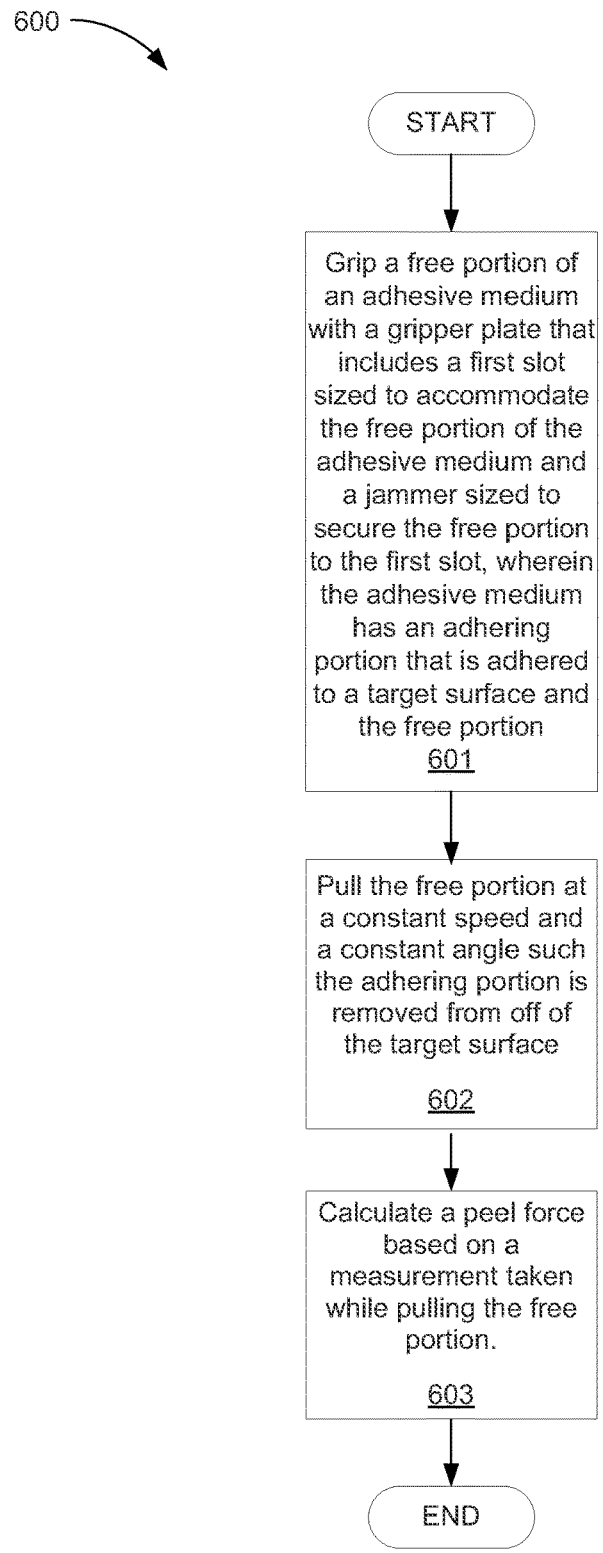
FIG. 6 is a flowchart of an example of a method for using an adhesive medium tester according to the principles described herein.

FIG. 6 is a flowchart of an example of a method for using an adhesive medium tester according to the principles described herein. The method includes gripping (601) a free portion of an adhesive medium with a gripper plate that includes a first slot sized to accommodate the free portion of the adhesive medium and a jammer sized to secure the free portion to the first slot, wherein the adhesive medium has an adhering portion that is adhered to a target surface and the free portion, pulling (602) the free portion at a constant speed and a constant angle such the adhering portion is removed from off of the target surface, and calculating (603) a peel force based on a measurement taken while pulling the free portion.

As mentioned above, the method includes gripping (601) a free portion of an adhesive medium with a gripper plate that includes a first slot sized to accommodate the free portion of the adhesive medium and a jammer sized to secure the free portion to the first slot, wherein the adhesive medium has an adhering portion that is adhered to a target surface and the free portion. In one example, a gripper plate is used to grip a free portion of an adhesive medium. In this example, the gripper plate includes a second slot sized to accommodate the free portion of the adhesive medium. The free portion of the adhesive medium is first inserted into the second slot as shown in FIG. 3. As mentioned above, the second slot provides additional bends in the free portion of the adhesive medium such that the friction between the gripper plate and the free portion of the adhesive medium is increased. As a result, the second slot helps to secure the free portion of the adhesive medium to the gripper plate. The free portion of the adhesive medium is then laid over the first slot. In this example, the free portion of the adhesive medium is laid past the first slot. The jammer is pressed into the first slot as shown in FIG. 3. As a result, the free portion of the adhesive medium is secured to the gripper plate such that the free portion of the adhesive medium does not slip from the gripper plate.

The method further includes, pulling (602) the free portion at a constant speed and a constant angle such the adhering portion is removed from off of the target surface. As mentioned above, a gripper plate secures a free portion of the adhesive medium. The gripper plate includes a connection to an elevator assembly. The elevator assembly moves along a column of the adhesive medium tester at a constant speed. As the elevator assembly moves along the column, the free portion of the adhesive medium is pulled at a constant speed and a constant angle such the adhering portion of the adhesive medium is removed from off of the target surface.

Additionally, the constant speed of the elevator assembly may affect the peel force of the adhesive medium. In one example, the elevator assembly moves along the column at a minimum constant speed. As a result, the free portion of the adhesive medium is pulled at a minimum constant speed and a constant angle such the adhering portion is removed from off of the target surface at a minimum constant speed.

In another example, the elevator assembly moves along the column at a medium constant speed. As a result, the free portion of the adhesive medium is pulled at a medium constant speed and a constant angle such the adhering portion is removed from off of the target surface at a medium constant speed.

In still another example, the elevator assembly moves along the column at a maximum constant speed. As a result, the free portion of the adhesive medium is pulled at a maximum constant speed and a constant angle such the adhering portion is removed from off of the target surface at a maximum constant speed.

The method includes, and calculating (603) a peel force based on a measurement taken while pulling the free portion. As mentioned above, a peel force may be measured to determine an adhesive medium's adhesive properties based on a constant angle and a constant speed. As mentioned above, a portion of the load cell sensor passes through a receiver in the sensor support block. In this example, the portion of the load cell sensor is held captive in the beveled impression of the receiver. While pulling a free portion of the adhesive medium at a constant speed and a constant angle such that the adhering portion is removed from off of the target surface, the tension increases on the load cell sensor. As the tension increases on the load cell sensor, the load cell is compress against the beveled impression on the receiver. As a result, the load cell sensor converts the force applied to the load cell sensor applied by the sensor support block into a voltage. Further, a converter module is used to read the voltage and convert the voltage into a force. As a result, a peel force may be calculated to determine an adhesive medium's adhesive properties based on a constant angle and a constant speed.

The preceding description has been presented to illustrate and describe examples of the principles described. This description is not intended to be exhaustive or to limit these principles to any precise form disclosed. Many modifications and variations are possible in light of the above teaching.

What is claimed is:
1. An apparatus for testing a peel force of an adhesive medium, said apparatus comprising:
    an elevator assembly slidably connected to a column, said elevator assembly comprising a connection to a gripper plate; and
    said gripper plate comprising a first slot sized to accommodate a free portion of an adhesive medium and a jammer sized to secure said free portion of said adhesive medium in said first slot.

2. The apparatus of claim 1, wherein said gripper plate further comprising:
- a second slot sized to accommodate said free portion of said adhesive medium to further secure said free portion of said adhesive medium; and
- a hook bend at an end of said gripper plate with a receptacle;
- wherein said hook bend at said end of said gripper plate with said receptacle allows a load cell sensor and a pull rod to be attached to said gripper plate.

3. The apparatus of claim 2, wherein said hook bend at said end of said gripper plate with said receptacle allows said connection to accommodate a number of differently sized gripper plates to accommodate a number of adhesive mediums.

4. The apparatus of claim 2, wherein said elevator assembly further comprises a sensor support block to secure said load cell sensor to said elevator assembly, wherein said sensor support block swivels on pins to self-align with a free portion of said adhesive medium.

5. The apparatus of claim 2, wherein said load cell sensor is positioned to measure a peel force of said adhesive medium from a target surface.

6. The apparatus of claim 5, wherein said load cell sensor comprises a convertor module to convert said peel force into a voltage.

7. The apparatus of claim 1, further comprising an electric motor positioned to move said elevator assembly along said column.

8. The apparatus of claim 7, further comprising controls to control a speed of said electric motor;
- wherein said controls allow said electric motor to move said elevator assembly along said column at a variety of speeds.

9. A system for testing a peel force of an adhesive medium, said system comprising:
- an elevator assembly slidably connected to a column, said elevator assembly comprising a connection to a gripper plate;
- said gripper plate comprising a first slot sized to accommodate a free portion of an adhesive medium and a jammer sized to secure said free portion of said adhesive medium to said first slot; and
- a sensor support block to secure a load cell sensor to said elevator assembly;
- wherein said sensor support block swivels on pins to self-align with a free portion of said adhesive medium.

10. The system of claim 9, wherein said elevator assembly is positioned to move along said column to cause an adhering portion of said adhesive medium that is adhered to a target surface to be pulled away from a target surface at a constant angle.

11. The system of claim 9, wherein said gripper plate further comprising:
- a second slot sized to accommodate said free portion of said adhesive medium to further secure said free portion of said adhesive medium; and
- a hook bend at an end of said gripper plate with a receptacle;
- wherein said hook bend at said end of said gripper plate with said receptacle allows said load cell sensor and a pull rod to be attached to said gripper plate.

12. The system of claim 9, wherein said load cell sensor comprises a convertor module to convert a peel force into a voltage.

13. The system of claim 9, further comprising an electric motor positioned to move said elevator assembly along said column.

14. The system of claim 13, further comprising controls to control a speed of said electric motor;
- wherein said controls allow said electric motor to move said elevator assembly along said column at a variety of speeds.

15. A method for testing a peel force of an adhesive medium, said method comprising:
- gripping a free portion of an adhesive medium with a gripper plate that includes:
  - a first slot sized to accommodate said free portion of said adhesive medium, wherein said adhesive medium has an adhering portion that is adhered to a target surface and said free portion;
  - a jammer sized to secure said free portion to said first slot; and
  - a connection to an elevator assembly, wherein said elevator assembly is movable along a column of an adhesive medium tester at a constant speed
- moving said elevator assembly along said column of said adhesive medium tester, thereby moving said gripper plate at a constant speed and thereby pulling said free portion at the constant speed and a constant angle such that said adhering portion is removed from said target surface; and
- calculating a peel force based on a measurement taken while pulling said free portion.

* * * * *

UNITED STATES PATENT AND TRADEMARK OFFICE
CERTIFICATE OF CORRECTION

PATENT NO. : 9,983,116 B2
APPLICATION NO. : 14/899530
DATED : May 29, 2018
INVENTOR(S) : Paul C. Landrum et al.

It is certified that error appears in the above-identified patent and that said Letters Patent is hereby corrected as shown below:

In the Claims

In Column 12, Line 38, in Claim 15, delete "speed" and insert -- speed; --, therefor.

Signed and Sealed this
Thirtieth Day of October, 2018

Andrei Iancu
*Director of the United States Patent and Trademark Office*